United States Patent [19]

Forse et al.

[11] Patent Number: 4,720,378

[45] Date of Patent: Jan. 19, 1988

[54] COATED COLORED INTAGLIATED ARTICLES

[75] Inventors: Sidney F. Forse, Macclesfield; Raymond C. Rowe, Congleton, both of England

[73] Assignee: Imperial Chemical Industries PLC, London, England

[21] Appl. No.: 885,756

[22] Filed: Jul. 22, 1986

Related U.S. Application Data

[63] Continuation of Ser. No. 347,480, Jul. 21, 1986, abandoned.

[30] Foreign Application Priority Data

Mar. 9, 1981 [GB] United Kingdom ............... 8107275
Sep. 9, 1981 [GB] United Kingdom ............... 8127301

[51] Int. Cl.$^4$ .............................................. A61K 9/20
[52] U.S. Cl. ........................................ 424/6; 424/467; 426/89; 426/103; 426/144; 426/293; 426/302; 426/383; 427/212; 427/218; 427/219; 427/220; 428/156; 428/161; 428/165; 428/172; 428/175; 428/212; 428/532

[58] Field of Search .................. 424/6, 15, 16, 31, 32, 424/34, 38, 35; 426/89, 103, 144, 293, 302, 383; 427/270, 271, 275, 212, 218–222; 428/156, 165, 172, 175, 913, 161, 212, 446, 532, 702, 703

[56] References Cited

U.S. PATENT DOCUMENTS

| | | | |
|---|---|---|---|
| 2,693,436 | 11/1954 | Spralding | 106/26 |
| 2,865,810 | 12/1958 | Sanders | 424/6 |
| 3,015,610 | 1/1962 | Sanders | 424/6 |
| 3,125,490 | 3/1964 | Hershberg | 424/6 |
| 4,353,887 | 10/1982 | Hess et al. | 424/15 |

OTHER PUBLICATIONS

Hagers Handbuch der pharmazeutischen Praxis, Springer Verlag, Berlin, 1971, 4th ed., vol. 7, pp. 693, 694 and 761–762.

*Primary Examiner*—Bruce H. Hess
*Attorney, Agent, or Firm*—Cushman, Darby & Cushman

[57] ABSTRACT

Coated articles, for example colored pharmaceutical tablets, bearing highlighted intagliations. The articles are colored intagliated articles bearing at least one film coat comprising at least one optically anisotropic substance, for example magnesium carbonate, and at least one film coating agent. Process for manufacturing said articles.

7 Claims, No Drawings

COATED COLORED INTAGLIATED ARTICLES

This is a continuation of application Ser. No. 347,480, filed July 21, 1986, which was abandoned upon the filing hereof.

This invention relates to coated coloured intagliated articles on which the intagliations are highlighted.

In order that the invention may be the more easily comprehended, two expressions used in this specification will now be defined: "intagliated article"—The word "intagliated" is related to the word "intaglio", which essentially means a figure or mark cut into any solid material. In one dictionary the word "intagliated" is defined as "incised" or "engraved". In the present specification the expression "intagliated article" means a solid article which has at least one figure, mark or notation, or any combination thereof, formed on the surface of the article by a compression punching, incision or engraving procedure, or by any other procedure which produces a like effect. "optically anisotropic substance"—An anisotropic substance is one which shows differences of property or effect in different directions. As it is used in this specification, the expression "optically anisotropic substance" means any substance which exhibits different refractive indices in different directions and which has a minimum refractive index not greater than 2.00.

Various methods are used in the pharmaceutical industry for putting product names, active ingredient information, company identifying marks, and/or like information, on the surface of unit dosage forms such as tablets. For example, one known method involves applying printed information or the like on to coated unit dosage forms, for example film coated tablets. Another method involves the use of intagliated unit dosage forms where the information or the like is presented on the surface of the dosage forms in the form of intagliations. In the said method involving printed information or the like, the information or the like can be applied in the form of one or more colors. However, printing is a relatively difficult, slow and costly procedure, and it involves the use of specialised machinery. By contrast, the process of this invention involves the use of coating apparatus (different versions of which are widely used in industry), it is a cheap and rapid process, and the products obtained are superior to those obtained by the said method involving printing. In the said known method involving intagliations, it has not been possible heretofore to produce intagliated unit dosage forms in which the intagliations are in a different colour from the remainder of the dosage form. The present invention remedies that deficiency.

We have found that if a colored (i.e. non-white) intagliated tablet (which may or may not already bear a film coat) is coated in a side-vented perforated coating drum with a film coat comprising an optically anisotropic substance and a film coating agent, the colour of the non-intagliated part of the tablet is very little changed from the original color, but the intagliations become coloured in a contrasting manner, and therefore they are highlighted. We believe that the scientific explanation for the result achieved may be as follows, but it is to be understood that we are not certain that this explanation is the correct one, and the scope of this invention is in no way to be limited by this explanation: during the coating process the optically anisotropic substance orientates itself in the film coat over the non-intagliated part of the tablet so that its refractive index is similar to that of the said film coat, that is, it appears essentially transparent; in the intagliations the optically anisotropic substance orientates itself in the film coat so that its refractive index exceeds that of said film coat, that is, it appears relatively opaque. Thus, the net effect is that the intagliations show up in a distinctive and attractive way against a colored background, and the intagliated information is much easier to read.

It is known to include an optically anisotropic substance such as calcium carbonate, magnesium carbonate, sucrose or lactose in film coating compositions, but it is not known, nor is it obvious, to apply such film coating compositions to colored intagliated articles, for example coloured intagliated tablets, in order to highlight the intagliations.

The present invention is capable of wide application, and it is to be understood that it is not solely restricted to the pharmaceutical field. Thus, for example, it can be applied in the veterinary field, for example in the preparation of boluses (i.e. veterinary tablets), or in the confectionery field, for example in the preparation of sugar confectionery (i.e. sweets or candy), and in other fields where it is desirable to have intagliated articles in which the intagliations are highlighted.

It is to be understood that in this specification a coloured article means a non-white article.

According to the invention there is provided a coloured solid article bearing at least one high-lighted intagliation, which comprises a coloured intagliated article bearing at least one film coat comprising at least one optically anisotropic substance having a minimum refractive index not greater than 2.00 and at least one film coating agent.

Prior to the application of the film coat which characterises this invention, the coloured intagliated article may be uncoated, for example it may be an uncoated medicinal tablet or bolus. Alternatively, prior to the application of the film coat which characterises this invention, the coloured intagliated article may bear at least one film coat, for example it may be a film coated medicinal tablet or bolus, or a film coated piece of sugar confectionery. The optional film coat, which may be present on the article prior to the application of the film coat which characterises this invention, may comprise any film coating agent or agents known in the art, for example a cellulose ether, for example methylcellulose, ethylcellulose, hydroxyethylcellulose, hydroxypropylcellulose, hydroxypropyl methylcellulose or sodium carboxymethylcellulose, or a mixture thereof, or cellulose acetate phthalate, hydroxypropyl methylcellulose phthalate, polyvinyl acetate, polyvinyl acetate phthalate, cellulose acetate, shellac or an acrylic resin, or a mixture thereof. The optional film coat may contain one or more adjuvants which are conventional in the film coating art, for example plasticisers, surface active agents and/or waxes. The optional film coat is applied in conventional manner using conventional apparatus (see below) and using either an organic solvent-based coating process, for example a process involving a mixture of methylene dichloride and methanol, or an aqueous coating process.

The colour, which characterises the intagliated article prior to the application of the film coat which characterises this invention, may be present throughout the article, or it may be applied to the surface of the article. Thus, a colored substance, for example a coloured medicinal or veterinary agent in the case of medicinal or veterinary intagliated articles, or a colouring agent, may be present throughout the article, or a colouring agent may be applied as such, or in the form of a colored film coat, to the surface of the article. Any conventional coloring agent which is approved for the general purpose in question, for example pharmaceutical purposes, may be used, for example iron oxide (red, yellow or black), carmine, natural dyes, for example turmeric or betacarotene, water-soluble dyes, for example tartrazine, or aluminium lakes of water-soluble dyes, or any mixture thereof, optionally in admixture with at least one opaque white pigment, for example titanium dioxide.

It is to be understood that the general description hereinafter concerning the optically anisotropic substances, film coating agents and colouring agents which can be used according to this invention is phrased in the singular for ease of reading and comprehension, but it applies also to mixtures of two or more of said optically anisotropic substances, film coating agents and/or colouring agents.

The optically anisotropic substance is used according to this invention in the form of a powder. As suitable optically anisotropic substances there may be mentioned, for example, white optically anisotropic substances, for example known transparent white pigments (also known as "extender" or "inert" white pigments), for example aluminium hydroxide, china clay (kaolin), talc, calcium carbonate or barium carbonate. Other suitable optically anisotropic substances are magnesium carbonate (light or heavy form), cane sugar (sucrose), lactose or tartaric acid. Alternatively, in the case of a medicinal tablet or bolus the medicinal or veterinary agent present therein may also be used as the optically anisotropic substance. That is, the medicinal or veterinary agent may be used in a dual role: as both the active agent in the tablet or bolus and as the optically anisotropic substance.

Suitable film coating agents for use in the film coat(s) which characterise(s) this invention are mentioned above.

As aforesaid, the optically anisotropic substance has a minimum refractive index not greater than 2.00. The choice of this substance depends upon the film coating agent applied therewith (i.e. in the same coating suspension) in that an optically anisotropic substance should be used which has a minimum refractive index which is the same as or similar to the refractive index of the film coating agent. It is an advantage to use an optically anisotropic substance which has a maximum refractive index which is as different as possible from its minimum refractive index, as this affords the best visual results. Details on typical materials which can be used according to the present invention are as follows:

| Film coating agents | Refractive index | |
|---|---|---|
| Methylcellulose | 1.50 | |
| Ethylcellulose | 1.47 | |
| Hydroxyethylcellulose | 1.51 | |
| Hydroxypropylcellulose | 1.56 | |
| Hydroxypropyl methylcellulose | 1.49 | |
| Sodium carboxymethylcellulose | 1.52 | |
| Cellulose acetate | 1.48 | |
| Shellac | 1.52 | |
| Acrylic resin | 1.48 | |
| Optically anisotropic substances | Refractive indices | |
| | Minimum | Maximum |
| Aluminium hydroxide | 1.50 | 1.56 |
| Kaolin | 1.56 | 1.57 |
| Talc | 1.54 | 1.59 |
| Calcium carbonate | 1.51 | 1.65 |
| Calcium sulphate | 1.57 | 1.61 |
| Barium carbonate | 1.53 | 1.68 |
| Magnesium carbonate | 1.51 | 1.70 |
| Cane sugar | 1.54 | 1.57 |
| α-Lactose | 1.52 | 1.57 |
| Tartaric acid | 1.50 | 1.61 |

The amount of optically anisotropic substance that is applied depends upon the degree of colour contrast required, the refractive indices of the substance, and its particle size. Thus, for example, in the case where the film coating agent is hydroxypropyl methylcellulose and intagliated tablets are used as starting material and themselves carry a film coat which is coloured with red or black iron oxide, the amounts of optically anisotropic substance which are used (expressed as % w/w of tablet weight) vary between 0.1 and 1.0%. In the case of corresponding tablets which carry a film coat coloured in more pastel shades, the said amounts vary between 0.5 and 5.0%. Approximately three times as much heavy magnesium carbonate, compared to light magnesium carbonate, is required to achieve the same effect.

The mixture of optically anisotropic substance and film coating agent may optionally contain one or more film coating adjuvants which are conventional in the film coating art, for example plasticisers, for example glycerol, propyleneglycol, polyethyleneglycol, diethyl phthalate, glyceryl monostearate or castor oil, and surface active agents, for example polyoxyethylene sorbitan monooleate ['Tween' 80 ('Tween' is a Trade Mark)], and waxes, for example beeswax or carnauba wax. Alternatively or additionally, the said mixture may optionally contain at least one coloring agent, for example one or more of the specific colouring agents mentioned above. By this means it is possible to obtain color combinations essentially similar to those described below in respect of the situation where there is present, on top of the film coat(s) comprising at least one optically anisotropic substance and at least one film coating agent, at least one additional film coat comprising at least one colouring agent.

According to a further feature of the invention, the articles of the invention may optionally carry, on top of the film coat(s) comprising at least one optically anisotropic substance and at least one film coating agent, at least one additional film coat. The latter (hereinafter "outer") film coat(s) comprise(s) one or more conventional film coating agents and optionally one or more conventional film coating adjuvants, as described hereinbefore, and it is or they are applied in conventional manner. The outer film coat(s) may in addition comprise at least one colouring agent so as to provide at least one coloured outer film coat. Where more than one such coat is present, each such coat may contain the same or different coloring agent(s). The net effect of this embodiment of the invention is that the colors in question [i.e. the color of the main body of the article and the color of the intagliations, on the one hand, and the color(s) of the outer film coat(s), on the other] interact in a subtractive manner [see Encyclopaedia Britannica, Micropaedia, Volume III, 1974, 22]. Numerous colour combinations are thus possible, the intagliations normally being seen as a pale version of the colour of the outer coat(s). If the colour of the main body of the article and that of the outer film coat(s) are so-called complementary colours (see above reference), the main body of the article is seen as black and the intagliations are seen as a pastel color [i.e. a pale version of the color of the outer coat(s)].

According to one embodiment of this invention, therefore, there is provided a colored intagliated article consisting of:
(a) a first colored intagliated article, which carries
(b) at least one film coat which comprises at least one optically anisotropic substance, at least one film coating agent, and optionally at least one coloring agent of the same or a different color from that of the said first colored intagliated article, and, on the outside of this coat or these coats
(c) at least one film coat which comprises at least one film coating agent and at least one colouring agent of the same or a different color from that of said first colored intagliated article.

Another embodiment of this invention comprises a colored intagliated solid medicinal or veterinary unit dosage form, for example a tablet or bolus, comprising at least one medicinal or veterinary agent, characterised by at least one film coat comprising at least one optically anisotropic substance, at least one film coating agent, and optionally at least one film coating adjuvant which is known in the film coating art.

As indicated above, the present invention is widely applicable, and therefore the precise nature of the said medicinal or veterinary agent is not critical.

Another embodiment of this invention comprises a coloured intagliated piece of sugar confectionery falling under the general term sweets or candy, characterised by at least one film coat comprising at least one optically anisotropic substance, at least one film coating agent, and optionally at least one film coating adjuvant which is known in the film coating art.

It is to be understood that:
(a) the said film coat(s) comprising at least one optically anisotropic substance and at least one film coating agent, and
(b) any film coat(s) applied on top of the said film coat(s) (a), appear(s) transparent or translucent [except that, as indicated above, the film coat(s) (a) appear(s) opaque in the intagliations]. That is to say, as skilled persons will appreciate, in order to obtain the desired results according to the present invention it is necessary for the viewer to be able to see through the film coat(s) in question to a reasonable extent.

According to a further feature of the invention there is provided a process for the manufacture of a colored solid article bearing at least one highlighted intagliation, which comprises applying to a coloured intagliated article, which itself may be uncoated or coated, a film coating suspension comprising at least one optically anisotropic substance having a minimum refractive index not greater than 2.00 and at least one film coating agent, which process is carried out in a conventional film coating apparatus such that a rubbing action takes place between the articles being coated.

The colored intagliated article used as starting material may be produced in any known manner using known materials. For example, solid medicinal or veterinary unit dosage forms, for example tablets or boluses, may be produced in conventional manner using conventional excipients and the appropriate active agent(s).

The optically anisotropic substance and film coating agent, and any film coating adjuvant and/or colouring agent applied therewith, are applied in the form of a coating suspension which may be an organic solvent-based suspension, for example where the solvent is a mixture of methylene dichloride and methanol, or an aqueous suspension. When all of the ingredients are water-soluble, they should be applied in an organic solvent-based suspension. The film coating procedure is carried out using a conventional film coating apparatus or machine, for example a coating pan, or a coating drum, for example a side-vented perforated coating drum, or a so-called Wurster coating apparatus (a fluidized bed coating apparatus). It is to be understood that a rubbing action between the intagliated articles being coated, that is the rubbing action that usually takes place between articles being coated in any conventional film coating apparatus or machine, is an essential feature of the process of this invention.

The invention is illustrated but not limited by the following Examples (it is to be understood that the placebo tablets contained no medicinal agent, whereas the medicinal tablets contained a medicinal agent):

EXAMPLE 1

A batch of 50,000 200 mg. intagliated white tablets (a mixture of placebo tablets and medicinal tablets), coated with a film coat coloured with red iron oxide, was heated to 60° C. in a side-vented perforated coating drum (24 inch Accela-Cota machine; obtainable from Manesty Machines Ltd., Speke, Liverpool 24, England). 4 liters of a 5% w/v aqueous solution of hydroxypropyl methylcellulose ['Pharmacoat' (Trade Mark) 606, Shin-Etsu Chemical Company Limited, Tokyo, Japan], containing 1% w/v glycerol, and containing calcium carbonate (30 g.) suspended therein, were applied continuously at 50 ml./min. by means of a low pressure air-spray unit. The drum speed was kept at 16 rpm and the temperature of the inlet drying air at 60° C. When the suspension had all been applied, the drum was stopped and the tablets removed. There were thus obtained red-brown film coated tablets with intagliations highlighted in white.

EXAMPLE 2

The process described in Example 1 was repeated except that the tablets used as starting material had previously been coated with a film coat coloured with a mixture of carmine and titanium dioxide, and the coating suspension applied contained light magnesium carbonate (60 g.) in place of the calcium carbonate, and 1% w/v polyethyleneglycol in place of the glycerol. There were thus obtained pink film coated tablets with intagliations highlighted in white.

EXAMPLE 3

A batch of 50,000 200 mg. intagliated white tablets (a mixture of placebo tablets and medicinal tablets), coated with a film coat coloured with red iron oxide, was heated to 60° C. in a side-vented perforated coating drum (24 inch Accela-Cota machine). 10 liters of a 2% w/v solution of hydroxypropyl methylcellulose ('Pharmacoat' 606) in methylene dichloride:methanol (70:30 v/v) containing 0.4% w/v glycerol, and containing aluminium hydroxide (90 g.) suspended therein, were applied continuously at 250 ml./min. by means of a high pressure airless spray unit. The drum speed was kept at 20 rpm and the temperature of the inlet drying air at 60°

C. When the suspension had all been applied, the drum was stopped and the tablets removed. There were thus obtained red-brown film coated tablets with intagliations highlighted in white.

EXAMPLE 4

A batch of 50,000 200 mg. intagliated carmine coloured tablets (a mixture of coated placebo tablets and uncoated medicinal tablets) was heated to 60° C. in a side-vented perforated coating drum (24 inch Accela-Cota machine). 1 liter of a 5% w/v aqueous solution of hydroxypropyl methylcellulose ('Pharmacoat' 606) containing 1% w/v glycerol, and containing light magnesium carbonate (30 g.) dispersed therein, was applied continuously at 50 ml./min. by means of a low pressure air-spray unit. The drum speed was kept at 16 rpm and the temperature of the inlet drying air was kept at 60° C. When the suspension had all been applied, the drum was stopped and the tablets removed. There were thus obtained pink film coated tablets with intagliations highlighted in white.

EXAMPLE 5

To a batch of 50,000 200 mg. white placebo tablets were added approximately 100 coloured, film coated, intagliated tablets (a mixture of placebo tablets and medicinal tablets), some of which were coloured grey with intagliations highlighted in white and others of which were coloured carmine with intagliations highlighted in white (these tablets were obtained as described below). The resulting mixed batch of tablets was heated to 60° C. in a side-vented perforated coating drum (24 inch Accela-Cota machine). 1 liter of a 3.3% w/v aqueous solution of hydroxypropyl methylcellulose ('Pharmacoat' 606) containing tartrazine water-soluble yellow dye (1 g.) and 0.66% w/v glycerol (plasticiser) was applied continuously at 50 ml./min. by means of a low pressure air-spray unit. The drum speed was kept at 14 rpm and the temperature of the inlet drying air at 60° C. When the solution had all been applied, the drum was stopped and the tablets removed. There was thus obtained inter alia:
(i) green film coated intagliated tablets with the intagliations highlighted in pale yellow (from the original grey tablets), and
(ii) orange-brown film coated intagliated tablets with the intagliations highlighted in pale yellow (from the original carmine tablets).

The said grey and carmine film coated, intagliated tablets used in the above process were prepared from 80–650 mg. intagliated white tablets (a mixture of placebo tablets and medicinal tablets) which were first coated with a film coat which was coloured with either a mixture of black iron oxide and titanium dioxide or a mixture of carmine and titanium dioxide, respectively. The resulting coloured film coated tablets were then coated with a suspension comprising hydroxypropyl methylcellulose and light magnesium carbonate as described in Example 4. There were thus obtained the said highlighted grey tablets and carmine tablets, respectively.

EXAMPLE 6

To a batch of 50,000 200 mg. white placebo tablets were added approximately 100 differently coloured, film-coated, intagliated tablets (a mixture of placebo tablets and medicinal tablets) in which the intagliations were highlighted in white (the said colored tablets included some red-brown intagliated tablets which were obtained as described below). The resulting mixed batch of tablets was heated to 60° C. in a side-vented perforated coating drum (24 inch Accela-Cota machine). 1 liter of a 3.3% w/v aqueous solution of hydroxypropyl methylcellulose ('Pharmacoat' 606) containing Brilliant Blue FCF water-soluble dye (Food, Drugs and Cosmetics Blue No. 1; 0.25 g.) and 0.66% w/v glycerol (plasticiser) was applied continuously at 50 ml./min. by means of a low pressure air-spray unit. The drum speed was kept at 14 rpm and the temperature of the inlet drying air at 60° C. When the solution had all been applied, the drum was stopped and the tablets removed. There were thus obtained inter alia black film coated intagliated tablets with the intagliations highlighted in pale blue (obtained from the original red-brown intagliated tablets).

The said red-brown tablets were prepared from approx. 200–400 mg. intagliated white tablets which were first coated with a film coat which was coloured with red iron oxide. The resulting film coated tablets were then coated with a suspension comprising hydroxypropyl methylcellulose and light magnesium carbonate as described in Example 4. There were thus obtained the said red-brown intagliated tablets with the intagliations highlighted in white.

EXAMPLE 7

To a batch of 50,000 200 mg. white placebo tablets were added approximately 100 415 mg. red-brown film coated intagliated tablets (the latter tablets were a mixture of placebo tablets and medicinal tablets, and they were coated with a film coat which was coloured with red iron oxide). 1 liter of a 3.3% w/v aqueous solution of hydroxypropylmethylcellulose ('Pharmacoat' 606) containing Brilliant Blue FCF water-soluble dye (0.25 g.) and 0.66% w/v glycerol, and having light magnesium carbonate (30 g.) dispersed therein, was applied to the mixed batch of tablets in a side-vented perforated coating drum (24 inch Accela-Cota machine). The suspension was applied continuously at 50 ml./min. by means of a low pressure air-spray unit. The drum speed was kept at 16 rpm and the temperature of the inlet drying air at 60° C. When the suspension had all been applied, the drum was stopped and the tablets removed. There were thus obtained inter alia black film coated tablets with the intagliations highlighted in pale blue (obtained from the original red-brown film coated intagliated tablets).

What we claim is:

1. A pharmaceutical tablet having at least one highlighted intagliation, said article comprising a coloured base having an intagliated part and a non-intagliated part, said base bearing over the whole of its surface at least one film coating which includes at least one film-coating agent and at least one optically anisotropic substance having a minimum refractive index of less than 1.57 and minimum and maximum refractive indices which differ by at least 0.04, the refractive index of the film-coating agent being essentially the same as the minimum refractive index of the optically anisotropic substance, and the amount of optically anisotropic substance in the film coating being such that the film appears transparent over the non-intagliated parts of the article and opaque over the intagliated parts, whereby the intagliations are highlighted in white or a colour which contrasts with the base colour of the article.

2. A tablet as claimed in claim 1 in which the optically anisotropic substance is white.

3. A tablet as claimed in claim 2 in which the optically anisotropic substance is selected from the group consisting of aluminum hydroxide, talc, calcium carbonate, calcium sulphate, barium carbonate, cane sugar, magnesium carbonate, $\alpha$-lactose and tartaric acid.

4. A tablet as claimed in claim 1 in which the film coating agent is a cellulose ether.

5. A tablet as claimed in claim 1 which carries, on top of the said film coat, at least one outer film coat comprising at least one film coating agent.

6. A tablet as claimed in claim 5 in which the outer film coat comprises at least one colouring agent.

7. A tablet according to claim 1 containing a medicinal or veterinary agent as both the active ingredient and as the optically anisotropic substance in said film coat.

* * * * *